US00PP24804P2

(12) United States Plant Patent
Horvath

(10) Patent No.: US PP24,804 P2
(45) Date of Patent: Aug. 19, 2014

(54) ***PENSTEMON DIGITALIS* PLANT NAMED 'POCAHONTAS'**

(50) Latin Name: *Penstemon digitalis*
Varietal Denomination: Pocahontas

(71) Applicant: Brent Horvath, Fontana, WI (US)

(72) Inventor: Brent Horvath, Fontana, WI (US)

( * ) Notice: Subject to any disclaimer, the term of this patent is extended or adjusted under 35 U.S.C. 154(b) by 102 days.

(21) Appl. No.: 13/573,644

(22) Filed: Oct. 1, 2012

(51) Int. Cl.
*A01H 5/00* (2006.01)

(52) U.S. Cl.
USPC ..... Plt./465

(58) Field of Classification Search
USPC ..... Plt./465
See application file for complete search history.

*Primary Examiner* — Annette Para

(57) ABSTRACT

A new, distinct *Penstemon digitalis* plant as shown and described, characterized by dark foliage with purple red coloration in combination with tubular flowers of purple pink, on substantial plants.

2 Drawing Sheets

Latin name: *Penstemon digitalis*.
Cultivar name: 'Pocahontas'.

BACKGROUND OF THE INVENTION

The present invention relates to a new and distinct hybrid of *Penstemon digitalis* plant named 'Pocahontas' characterized by dark foliage with purple red coloration, in combination with tubular flowers of purple pink, on substantial plants. The new *Penstemon digitalis* was the result of a breeding program taking place in Hebron, Ill. since 2006. The female or seed parent was a *Penstemon digitalis* selection with dark burgundy red foliage while the male parent was *Penstemon digitalis* 'Pink Dawn', a short deep pink flowered selection. The selection of the new plant was due to its' dark foliage with purple red coloration in combination with tubular flowers of purple pink, on substantial plants. Asexual cutting and division propagation has been the means of reproduction. The intial cutting and division propagation has taken place at a nursery in Hebron, Ill. since 2009. The new *Penstemon digitalis* has shown to be stable and identical in reproduction to the parent after rooting over 5000 plants from 2009 to 2012.

SUMMARY OF THE INVENTION

The new *Penstemon digitalis* plant named 'Pocahontas' characterized by dark foliage with purple red coloration in combination with tubular flowers of purple pink, on substantial plants, have been observed to be unique and stable.

Plants of the new *Penstemon digitalis* can be compared to the male or pollen parent, *Penstemon digitalis* 'Pink Dawn', not patented. 1. The new plant height is typically 36" plus tall while *Penstemon digitalis* 'Pink Dawn' is typically 18-24" tall. 2. The new plant also has dark green or purple to red foliage much of the year while *Penstemon digitalis* 'Pink Dawn', has green foliage much of the year.

Plants of the new *Penstemon digitalis* can also be compared to plants of *Penstemon* hybrid 'Dark Towers', U.S. Plant Pat. No. 20,013, patented. 1. The new plant height is typically 36" plus tall while *Penstemon* hybrid 'Dark Towers' is typically 30" tall. 2. The new plant also has larger, deeper purple pink flowers while *Penstemon* hybrid 'Dark Towers', typically has smaller pink and white flowers. 3. The new plant also has two different *Penstemon digitalis* as its parents while *Penstemon* hybrid 'Dark Towers', has three different species involved in its parentage.

DESCRIPTION OF PHOTOGRAPHS

Figure 1:
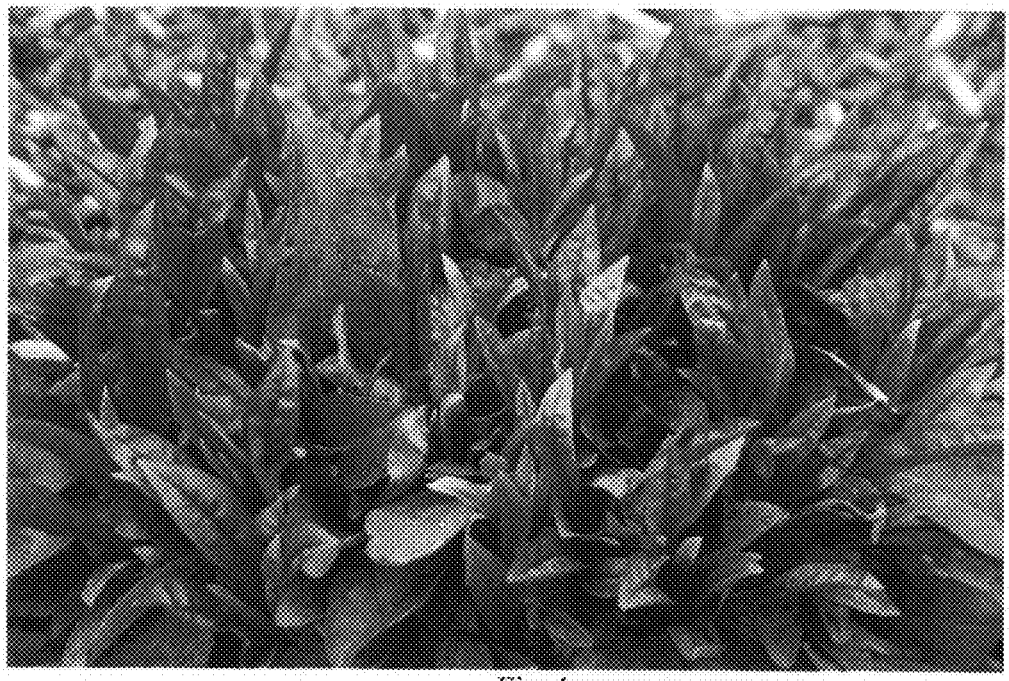
Figure 2:
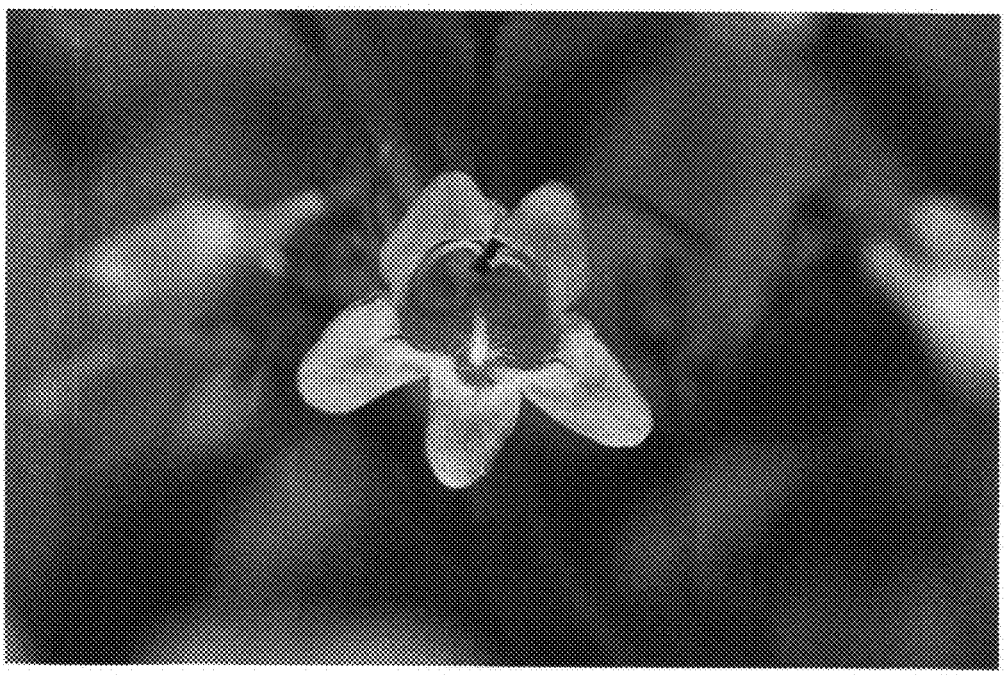
Figure 3:
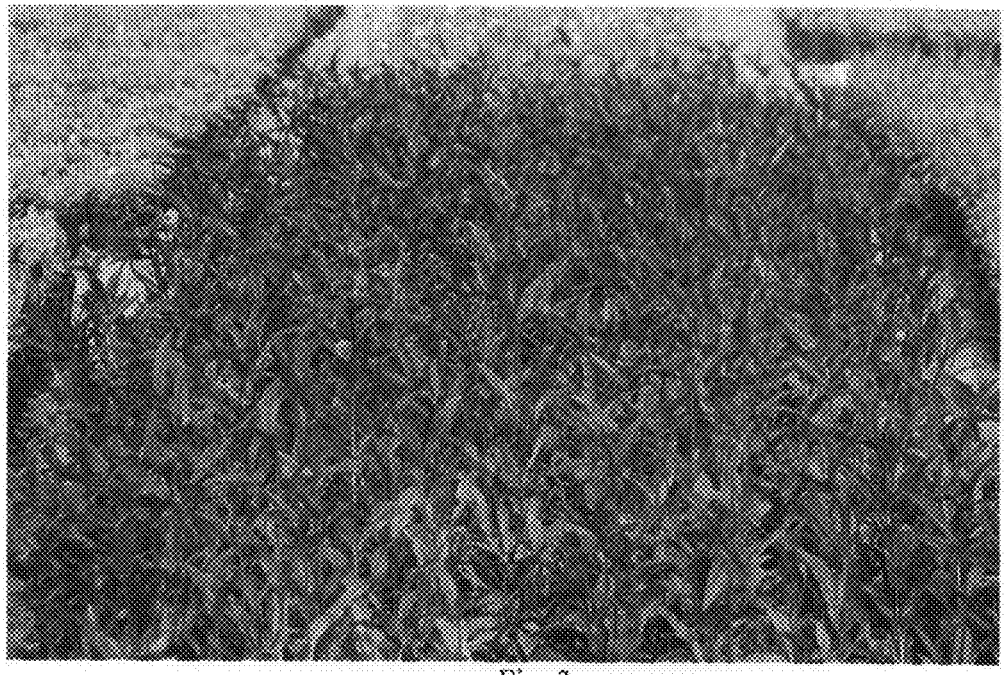
Figure 4:
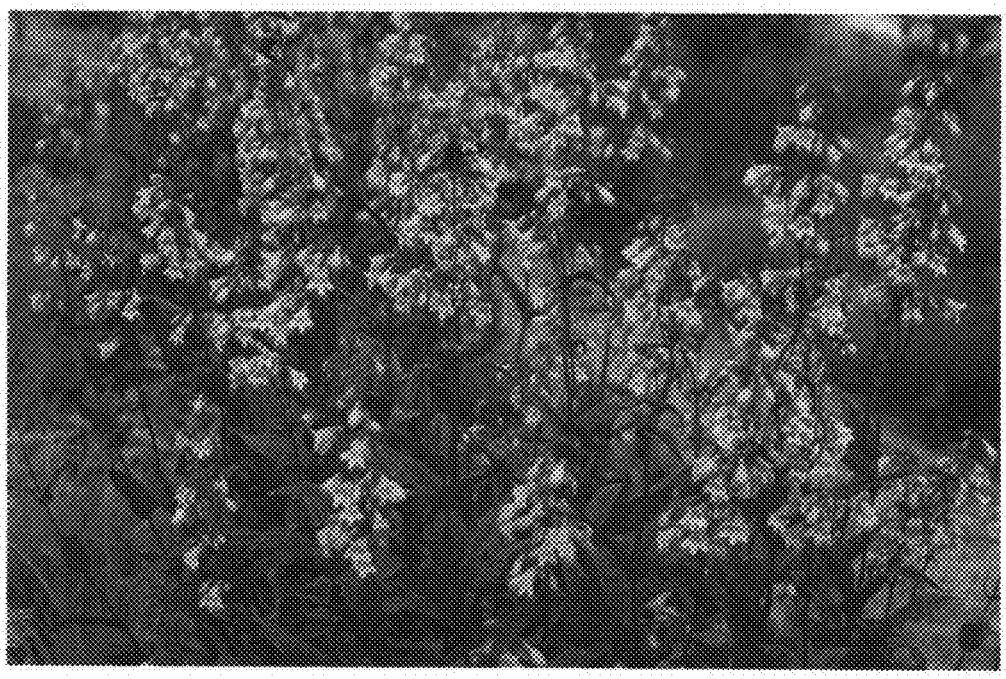

FIG. 1. New foliage in spring.
FIG. 2. A single flower in June.
FIG. 3. Budding plants in May.
FIG. 4. Blooming plants in June.

DETAILED BOTANICAL DESCRIPTION

In the following description, color references are made to The Royal Horticultural Society Colour Chart (2001). Plants used for the description were grown in the ground for two years at a nursery in Hebron, Ill. Measurements and numerical values represent averages of typical plants.

Botanical classification: *Penstemon digitalis* cultivar 'Pocahontas'.

Parentage: *Penstemon digitalis* 'Pink Dawn' as the male parent and *Penstemon digitalis* dark red leaved seedling as the female parent.

Propagation: Vegetative cuttings and division.

Plant description:

*Type*.—Herbaceous perennial. The overall habit of the new *Penstemon digitalis* is a basal rosette, with thick upright maroon red flower stems topped by tubular purple pink flowers on loose clusters in June.
*Hardiness*.—USDA zones 3-8.
*Plant height*.—90-100 cm.
*Plant width*.—80-90 cm.
*Stem*.—Diameter — up to 8 mm.
*Stem or basal branches*.—Length: 90-100 cm.
*Internodes*.—Number: up to 10, length: 9 cm.
*Stem coloration*.—Stem base color varies from purple color N 79 B and C, to green 146 C and D, the coloration at the top of the stem is 181 A.
*Stem texture*.—Smooth, glabrous.
*Roots*.—Fibrous, color not measured.

Foliage description:

*Type*.—Simple, sessile.
*Shape*.—Oblanceolate.

*Arrangement*.—Opposite.
*Leaf blade size*.—Length: up to 20 cm, Width: 6 cm.
*Margins*.—Serrate.
*Petiole size*.—Length: up to 7-9 cm, Diameter: 5 mm.
*Petiole color*.—181 A.
*Leaf apex*.—Acuminate.
*Leaf base*.—Oblique.
*Texture*.—Upper and lower surfaces: smooth, glabrous.
*Adaxial leaf color description*.—N 77 A.
*Abaxial leaf color description*.—N 79A.
*Venation pattern*.—Pinnate.
*Venation color*.—Upper N 77 A, lower N 79A.
*Lateral leaflet number*.—Up to 10 pair per stem.
*Lateral leaflet length*.—Up to 15 cm.
*Lateral leaflet width*.—Up to 3 cm.
*Lateral leaflet shape*.—Lanceolate.
*Adaxial lateral leaflet color*.—N 77 A on the new red growth, lightening to 137 A.
*Abaxial lateral leaflet color*.—N 79A on the new red growth, lightening to 137 D.

Flower description:
*Inflorescence type*.—Panicle.
*Panicle size*.—Length: 24 cm tall, width: 10 cm.
*Peduncle color*.—181 A.
*Peduncle size*.—Length: 15 cm, diameter: 2 mm.
*Peduncle texture*.—Smooth, glabrous.
*Pedicel size*.—Length: 5-13 mm, diameter: 1 mm.
*Pedicel color*.—N 77 A.
*Flower bud*.—Size: length: 23 mm, diameter: 7 mm.
*Flower bud surface*.—Slightly pubescent.
*Flower bud shape*.—Ovoid, tubular, constricted at the base.
*Flower bud color*.—N 82 A.
*Corolla description*.—5 petals fused into a tube, constricted at the base.
*Petal apex*.—Entire, obtuse.
*Petal base*.—Fused, constricted.
*Petal margin*.—3 lower lobes and 2 upper lobes.
*Petal texture*.—Outer surface: glandular, inside surface: smooth.
*Petal color outer surface*.—Is color N 82 A.
*Petal color inside surface*.—Color is N 82 B.
*Calyx shape*.—Stellate, campanulate.
*Calyx size*.—Length: 6 mm, Width: 11 mm.
*Calyx color*.—181 A.
*Sepal arrangement*.—Fused.
*Sepal size*.—Length: up to 8 mm, diameter: 2-3 mm at base coming to a point.
*Sepal quantity*.—5.
*Sepal shape*.—Lanceolate, apex: acute, base: cuneate, margin: entire.
*Sepal texture*.—Upper and lower surfaces: smooth, glabrous.
*Sepal color*.—Adaxial color N 77 A, Abaxial color N 77 A.
*Flower type*.—Perfect.
*Flower shape*.—Tubular, bilabiate, with 5 petals having 2 upper lobes and three lower lobes, fused into a tube and constricted at the base.
*Flower color*.—N 82 A outside, N 82 B inside.
*Flower size*.—Length: 25 mm, width: 14 mm.
*Flower number*.—80 per panicle, 3000 per plant.
*Number of flowering stems*.—38.
*Bloom period and duration*.—Beginning of June in Hebron, Ill.
*Flower longevity and duration on the plant*.—Approximately 3 weeks.
*Flower longevity and duration cut*.—Not measured.
*Scent*.—None.

Reproductive organs:
*Stamen*.—Quantity: 4, length: 24 mm, diameter: close to 1 mm.
*Anther*.—Quantity: 4, length: 2 mm, diameter: 1 mm.
*Anther shape*.—Oval, color not measured.
*Filament*.—Cream colored at tip near anther, pink at the base.
*Pollen*.—Present, color: white.
*Pistil*.—Number: 1, length: 24 mm, width: 2-3 mm.
*Stigma shape*.—Conical.
*Style*.—Number: 1, length: 20 mm.
*Ovaries*.—Not measured.
*Fruit*.—Capsule, 10 mm long, 5 mm wide, glabrous, color 166 A.

Disease resistance: Resistance to diseases common to *Penstemon* has not been observed on plants grown under nursery conditions.

I claim:

1. A new, distinct *Penstemon* plant as shown and described, characterized by dark foliage with purple red coloration in combination with tubular flowers of purple pink, on substantial plants.

* * * * *